United States Patent [19]
Kieval et al.

[11] Patent Number: 5,749,906
[45] Date of Patent: *May 12, 1998

[54] DUAL CHAMBER PACING SYSTEM AND METHOD WITH CONTINUAL ADJUSTMENT OF THE AV ESCAPE INTERVAL SO AS TO MAINTAIN OPTIMIZED VENTRICULAR PACING FOR TREATING CARDIOMYOPATHY

[75] Inventors: Robert S. Kieval, Golden Valley; Michael F. Hess, Minneapolis, both of Minn.

[73] Assignee: Medtronic, Inc., Minneapolis, Minn.

[*] Notice: The term of this patent shall not extend beyond the expiration date of Pat. No. 5,650,252.

[21] Appl. No.: 753,867

[22] Filed: Dec. 3, 1996

Related U.S. Application Data

[62] Division of Ser. No. 391,883, Feb. 21, 1995, Pat. No. 5,626,620.

[51] Int. Cl.$^6$ .................................................. A61N 1/36
[52] U.S. Cl. ........................................................... 607/9
[58] Field of Search ............................. 607/9, 25, 27, 607/28, 17

[56] References Cited

U.S. PATENT DOCUMENTS

| | | |
|---|---|---|
| 4,428,378 | 1/1984 | Anderson et al. |
| 4,878,497 | 11/1989 | Callaghan et al. ............... 607/28 |
| 5,052,388 | 10/1991 | Silvula et al. |
| 5,144,949 | 9/1992 | Olson ............................... 607/17 |
| 5,282,838 | 2/1994 | Hauser et al. .................... 607/9 |
| 5,334,220 | 8/1994 | Sholder ............................ 607/9 |
| 5,340,361 | 8/1994 | Sholder ............................ 607/24 |
| 5,411,524 | 5/1995 | Rahul ............................... 607/4 |
| 5,507,782 | 4/1996 | Kieval et al. ..................... 607/9 |
| 5,514,163 | 5/1996 | Markowitz et al. .............. 607/9 |
| 5,527,347 | 6/1996 | Shelton et al. ................... 607/9 |
| 5,534,016 | 7/1996 | Boute ............................... 607/9 |

FOREIGN PATENT DOCUMENTS

| | | | |
|---|---|---|---|
| 0 597 728 A2 | 5/1994 | European Pat. Off. | ........ A61N 1/368 |
| 0 681 850 A2 | 5/1994 | European Pat. Off. | ........ A61N 1/368 |
| WO 94/11061 | 5/1994 | WIPO | ............................ A61N 1/39 |

OTHER PUBLICATIONS

Fananapazir, et al., "Impact of Dual Chamber Permanent Pacing in Patients with Obstructive Hypertrophic Cardiomyopathy with Symptoms Refractory to Verapamil and B-Adrenergic Blocker Therapy", Circulation, vol. 8, No. 6, Jun., 1992 pp. 2149-2161.

McDonald, Kehheth et al., "Permanent Pacing as Treatment for Hypertrophic Cardiomyopathy", The American Journal of Cardiology, vol. 68 Jul. 1991, pp.108-110.

(List continued on next page.)

Primary Examiner—Jeffrey R. Jastrzab
Attorney, Agent, or Firm—Harold R. Patton; Michael B. Atlass

[57] ABSTRACT

A dual chamber pacemaker is provided having capability for adjusting the AV escape interval so as to optimize the timing of delivered ventricular pace pulses for therapy of patients with cardiomyopathy. The pacemaker system continually monitors to determine when a delivered pace pulse results in a fusion beat, and periodically adjusts the AV escape interval in accordance with the percentage or rate of incidence of such fusion beats. In one specific embodiment, the pacing system determines the percentage of delivered ventricular pace pulses which are followed by fusion beats over a predetermined number of intervals, and decrements AV escape interval when such percentage is not below a predetermined minimum. The pacing system also periodically increments AV escape interval when the rate of fusion beats is acceptable, thereby providing a closed loop system for maintaining the AV interval at an optimally long value consistent with maximizing full capture by delivered ventricular pace pulses. In another embodiment, the V—V escape interval of a non-tracking mode pacemaker is controlled to optimize pre-excitation of the ventricle.

11 Claims, 8 Drawing Sheets

OTHER PUBLICATIONS

McAreavey, Dorothea et al., "Altered Cardiac Hermodynamic and Electrical State in Normal Sinus Rhythm after Chronic Dual–Chamber Pacing for Relief of Left Ventricular Outflow Obstruction in Hyptrophic Cardiomyopathy" American Journal of Cardiology. vol. 7, Sep. 1992, pp. 651–656.

McAreavey, Dorothea et al., "Effects of Dual Chamber Pacing in Hypertrophic Obstructive Cardiomyopathy," The Lancet, vol. 339, May 1992, pp. 1318–1323.

Jeanrenaud, Xavier et al., "Effects of Dual–Chamber Pacing in Hypertrophic Cardiomyopathy without Obstruction", The Lancet, vol. 3339, May 1992 pp. 1318–1323.

Seidelin, P.H., "Effects of Dual–Chamber Pacing in Hyper Cardiomyopathy without Obstruction", The Lancet, vol. 340 Aug., 1992, pp. 369–370.

DUAL CHAMBER PACING SYSTEM AND METHOD WITH CONTINUAL ADJUSTMENT OF THE AV ESCAPE INTERVAL SO AS TO MAINTAIN OPTIMIZED VENTRICULAR PACING FOR TREATING CARDIOMYOPATHY

This is a divisional of application Ser. No. 08/391,883 filed on Feb. 21, 1995 now U.S. Pat. No. 5,626,620.

BACKGROUND OF THE INVENTION

This invention relates to cardiac pacing systems and methods generally and, in particular, to dual chamber cardiac pacing systems and methods for delivering ventricular pacing pulses synchronized to atrial signals so as to benefit patients with cardiomyopathy and other forms of congestive heart failure and, in particular, patients with Hypertrophic Obstructive Cardiomyopathy (HOCM).

Hypertrophic Obstructive Cardiomyopathy is characterized by a narrowed left ventricular outflow tract (LVOT), which causes a significant increase in the subaortic pressure gradient. The narrowed LVOT is caused by an increased thickness of the interventricular septum which obstructs blood flow during systole, or at the time of cardiac output.

Symptomatic improvement of patients with HOCM can be obtained in some cases with the use of standard pharmacotherapy. However, drugs in use for this therapy have disadvantages which have been cited in the literature. Likewise, surgical intervention, e.g., septal myectomy or mitral valve replacement, is another optional treatment. However, such surgical treatments carry a significant operative mortality and have not been shown to alter the natural history of the disease. See, "Permanent Pacing As Treatment For Hypertrophic Cardiomyopathy," by Kenneth M. McDonald et al., American Journal of Cardiology, Vol. 68, pp. 108–110, July 1991.

The value of dual chamber cardiac pacing and treatment of patients suffering from HOCM has been recognized in the literature. Modern multiple-mode, dual-chamber cardiac pacemakers are designed to maintain AV synchrony for damaged or diseased hearts that are unable to do so on their own. For example, a DDD pacemaker has electrical connections to both the atrium and the ventricle, senses electrical signals in both chambers of the patient's heart, and delivers atrial pacing stimuli in the absence of signals indicative of natural atrial depolarization, and ventricular pacing stimuli in the absence of signals indicative of natural ventricular depolarization. Such a dual chamber pacemaker maintains the AV synchrony of the heart by delivering ventricular pace pulses at a controlled AV interval following each atrial event.

Studies have indicated that patients suffering from HOCM may benefit from a pacing treatment wherein a ventricular pace pulse is delivered in a specific timed relationship to the sensed or paced atrial depolarization. In particular, if the right ventricular apex is paced before spontaneous atrio-ventricular conduction activates the left ventricle, the ventricular and ventricular septal activation patterns are altered. This reduces leftward motion of the Septum, thereby reducing the LVOT obstruction and subaortic pressure gradient.

The literature uniformly acknowledges the potential advantages of synchronized A–V pacing for HOCM patients, stressing the importance of achieving ventricular capture. Causing "complete ventricular capture" is important to obtain the above-described septal movement, while selecting the longest AV delay that results in complete ventricular capture is important in order to maximize the atrial contribution to ventricular filling. See U.S. application Ser. No. 08/214,933, filed Mar. 17, 1994, Method and Apparatus For Dual Chamber Cardiac Pacing, assigned to Medtronic, Inc., and the literature articles referenced therein. The delivered pace pulse should provide "pre-excitation," i.e., depolarization of the ventricular apex before the septum. This altered pattern of septal contraction, as well as optimal left ventricular filling, is generally recognized as being important to this mode of pacemaker treatment. Further, it appears to be established that such synchronized AV pacing provides HOCM patients a long term benefit, i.e., the benefit remains even after cessation of pacing, since such AV pacing causes a reduction in the obstruction of the LVOT which persists in sinus rhythm after cessation of pacing.

The literature suggests that the AV escape interval should be set at the longest duration that maintains ventricular capture at different exercise levels. See the above-cited McDonald article. It has been suggested that the AV escape interval which allows for maximal pre-excitation of the ventricle by the pacing pulse can be selected by determining the AV escape interval that produces the widest paced QRS complex duration. See "Impact of Dual Chamber Permanent Pacing in Patients With Obstructive Hypertrophic Cardiomyopathy With Symptoms Refractory to Verapamil and β-Adrenergic Blocker Therapy," by Fananapazir et al., Circulation, Vol. 8, No. 6, June 1992, pp. 2149–2161.

In the referenced U.S. application assigned to Medtronic, Inc., the pacemaker periodically checks to determine a value of intrinsic AV conduction time (AVC) and subtracts therefrom a ventricular sense offset interval (VSO) to get the AV escape interval. After a waveform of the ventricular depolarization resulting from complete capture is noted and recorded for comparison, the AV escape interval is set to a lengthened value, resulting in one or more ventricular sense events. The value of AVC is determined as the time difference between the atrial event and the sensed R-wave. Following this, the pacemaker AV escape interval is reduced further until the pacemaker finds an R wave with a waveform that indicates good capture. The difference between AVC and the capture value of A–V is VSO, and the pacemaker thereafter sets AV=AVC–VSO.

The prior art techniques for synchronous pacing of HOCM patients recognize the necessity to periodically evaluate the AV delay, or AV escape interval. The patient's spontaneous atrio-ventricular conduction time generally will change with heart rate, i.e., from rest to exercise. Moreover, simultaneous drug treatment such as beta blockers may also modify AV conduction time and require renewed evaluation of the AV delay. The importance of periodically making an accurate determination of the optimized AV interval thus takes on significance. If the AV delay is adjusted to a value which is too short, in order to ensure complete ventricular capture, the atrial contribution to ventricular filling is compromised. However, if the AV escape interval is adjusted to too great a value, ventricular capture is compromised, and there may be episodes of no ventricular pacing or the ventricular pace may not contribute the best possible reduction of the LVOT obstruction. Accordingly, it is important in this therapy to be able to continuously or periodically adjust the AV escape interval to optimize it for HOCM therapy.

Accordingly, there is a substantial need for an improved method of treating patients having cardiomyopathy or certain forms of congestive heart failure, and a system for carrying out such treatment. The treatment of this invention embodies pacing the patient's ventricle in a timed relationship to the anticipated depolarization which would otherwise occur due to spontaneous atrio-ventricular conduction. While the preferred embodiment involves synchronized dual chamber pacing and adjustment of the AV escape interval, it is within the broader scope of the invention to deliver ventricular pace pulses that have a controlled timing so as to optimize pre-excitation of the ventricle, whether or not the ventricular pace pulses are synchronized to atrial events. Further, while the preferred embodiment is illustrated in terms of treating HOCM, the system and method of this invention are also applicable to treatment of dilated cardiomyopathy and certain forms of congestive heart failure.

SUMMARY OF THE INVENTION

The pacemaker system and method of this invention are based on the observation that when a ventricular pace pulse is delivered with a timing that results in a fusion or near fusion beat, there is a detectable change in the characteristics of the evoked QRS. In the practice in this invention, such fusion condition can be detected by discriminating a relative change in duration of the evoked QRS signal, a relative change in QRS amplitude, or a change in the QRS morphology, or a change in T-wave characteristics.

In accordance with a preferred embodiment of this invention, the pacemaker system detects fusion beats and monitors the number of fusion beats which occur over a predetermined time interval or number of pacemaker cycles, and determines whether this percentage is acceptable. The acceptable percentage may be zero, i.e., no fusion beats are acceptable, or it may be a suitable non-zero small percentage. When an unacceptable fusion percentage is determined, the pacemaker automatically adjusts AV delay to a lesser value, i.e., a value which restores continuous capture by delivered synchronous ventricular pace pulses. When the pacemaker operation has proceeded for a predetermined time or cycle interval without any determination of non-acceptable fusion beats, the pacemaker increments AV interval toward the fusion value, so as to continually adapt the value toward the longest possible value consistent with avoiding fusion. In another embodiment, the V—V escape interval of a non-tracking mode pacemaker is controlled to optimize pre-excitation of the ventricle.

DETAILED DESCRIPTION OF THE PREFERRED EMBODIMENTS

Figure 1:
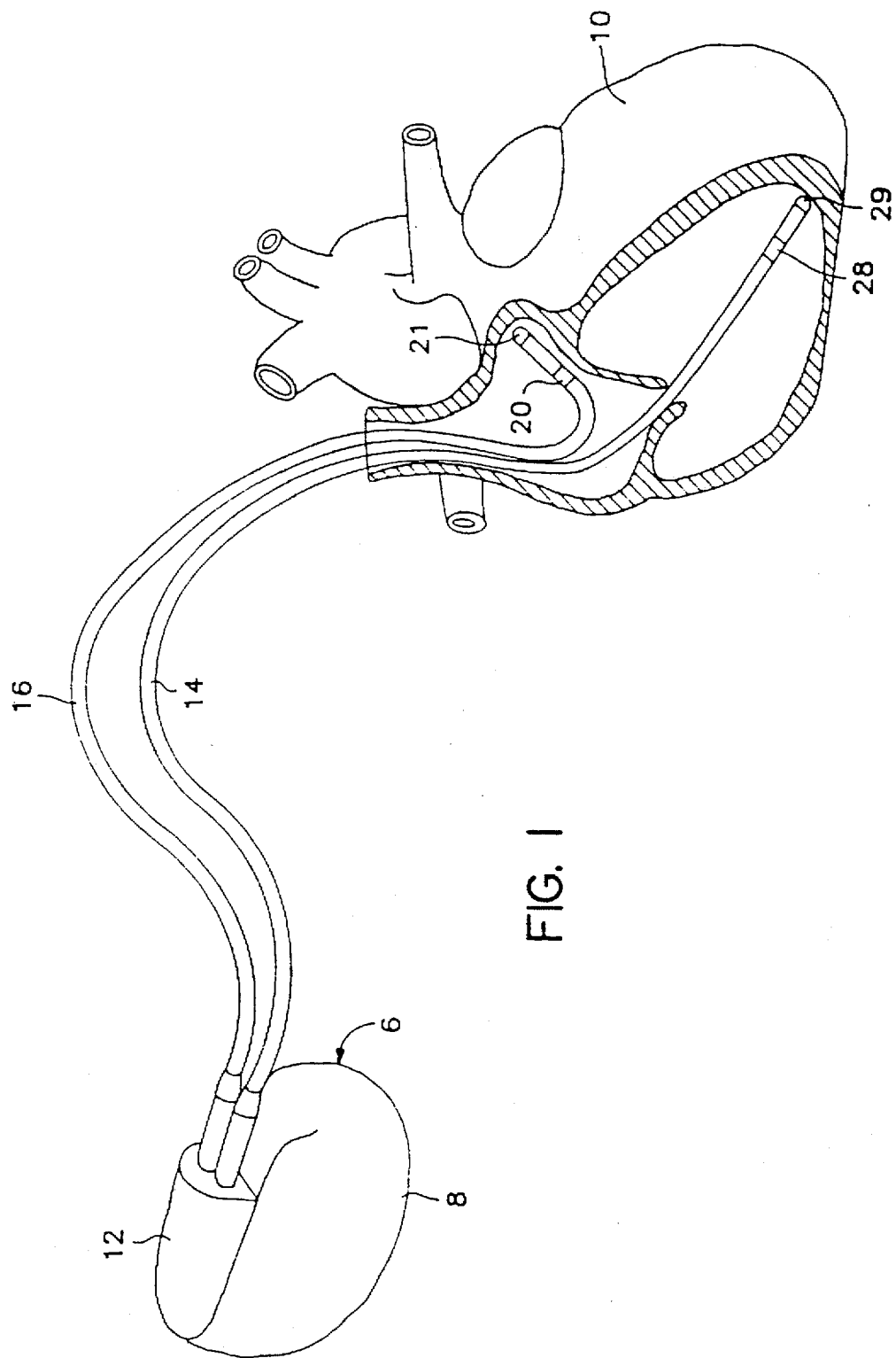
FIG. 1 is a perspective representation of the pacemaker system of this invention showing an implantable pacemaker connected to a patient's heart.

FIG. 1 illustrates the external configuration of a dual chamber pacemaker 6, which is provided with a hermetically sealed enclosure 8, typically fabricated of biocompatible metal such as titanium. Mounted to the top of the enclosure 8 is a connector block assembly 12, which receives electrical connectors located on the proximal ends of leads 14 and 16. Lead 16 is an atrial pacing lead, carrying two electrodes 20 and 21. Electrodes 20 and 21 are used both to sense atrial depolarizations and to deliver atrial pacing pulses. Atrial pacing pulses may be delivered between electrode 20 and electrode 21 or between electrode 21 and the housing 8 of the pacemaker 6. Sensing of atrial depolarizations may occur between electrode 20 and electrode 21 or between either of electrode 20 and 21 and the housing 8 of the pacemaker 6.

Similarly, lead 14 represents a ventricular bipolar pacing lead, carrying two electrodes 28 and 29. As discussed above in conjunction with atrial lead 16, electrodes 28 and 29 are used to sense and pace the ventricle. Ventricular pacing may be accomplished between electrodes 29 and 28 or between electrode 29 and the conductive housing 8 of pacemaker 6. Sensing of ventricular signals, including depolarizations (QRS-waves) and repolarizations (T-waves) may be accomplished between electrodes 29 and 28 or between either of electrodes 29 and 28 and the housing 8 of the pacemaker 6.

As discussed in the present application, the preferred embodiments of the pacemaker 6 operate in a DDD or DDDR pacing mode, wherein pacing pulses are delivered to both atrium and ventricle and wherein atrial and ventricular depolarizations are both effective to inhibit delivery of the next scheduled pacing pulse in the chamber in which they are detected. While the present invention is believed optimally practiced in a pacemaker operating in DDD pacing mode, in some patients there may also be a benefit to operating the device in VDD or DVI mode, which provides ventricular pacing pulses synchronized only to sensed atrial depolarizations or only delivered to atrial pacing pulses, respectively, depending upon the specific underlying heart condition of the patient. However, DDD mode is expected to be the mode most widely used to practice the present invention.

Figure 2:
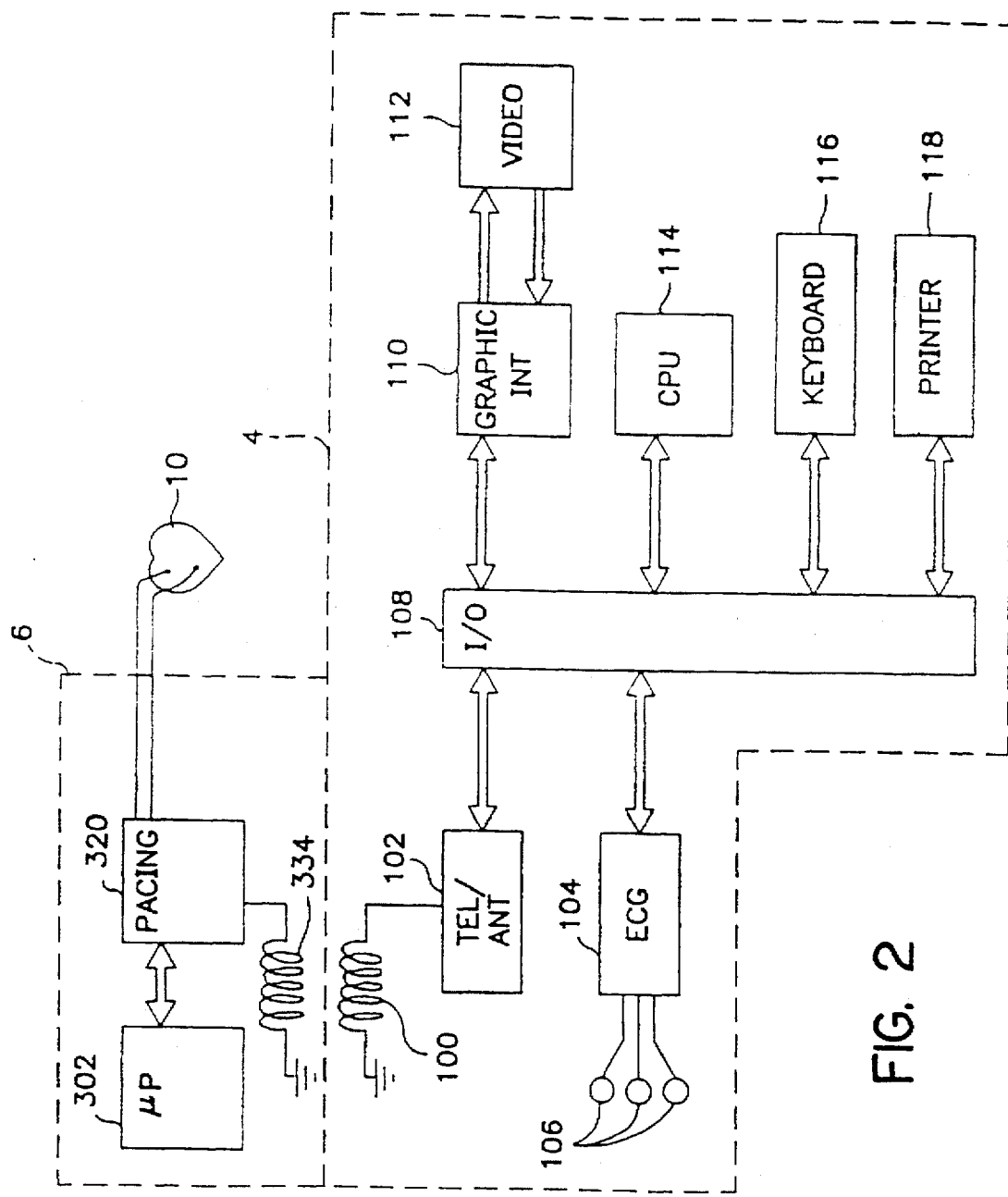
FIG. 2 is a block diagram of the pacemaker system of this invention, showing a pacemaker inter-connected with an external programmer and with ECG leads.

FIG. 2 illustrates the pacemaker 6 in block diagram form, coupled to a human heart 10, in conjunction with an external programmer/display apparatus corresponding to those typically employed to program modern, multi-programmable implantable pacemakers. Within the housing of the pacemaker are located the pacing circuitry 320, which includes circuitry performing all of the basic timing, stimulation and sensing functions of a cardiac pacemaker and a microprocessor circuit 302, which controls the timing intervals provided by the pacing circuitry 320. Pacing circuitry 320 also includes a bidirectional telemetry circuit coupled to an antenna 334, allowing transmission of information from external programmer 4 into the pacemaker 6 to modify its parameters and allowing transmission of information from the pacemaker 6 to the external programmer 4, again generally corresponding to telemetry and programming systems presently existing in commercially marketed multi-programmable in implantable pacemakers.

The programmer 4 also includes a corresponding antenna 100 coupled to a telemetry/antenna driver circuit 102 which serves to demodulate telemetry signals received from antenna 334 of the pacemaker, and to apply them in parallel or serial digital format to input output (I/O) unit 108, where they in turn may be applied to a video monitor 112 via graphic interface 110, and/or provided to central processing unit 114 and/or printer 118. Microprocessor 114 controls the operation of the programmer/display apparatus, and is responsive to physician entered commands via keyboard 116, for controlling programming signals sent to the pacemaker, as well as for controlling operation of the video display 112 and printer 118. Also illustrated is an ECG interface 104, coupled to three ECG electrodes 106 which can be placed upon the patient's body. ECG interface 104 provides sensed electrograms to input/output device 108, where they in turn may be provided to the video display 112, the central processing unit 114 or the printer 118. The ECG capability is used for treatment according to the method of this invention for a patient who is available for initial or subsequent programming.

Figure 3:
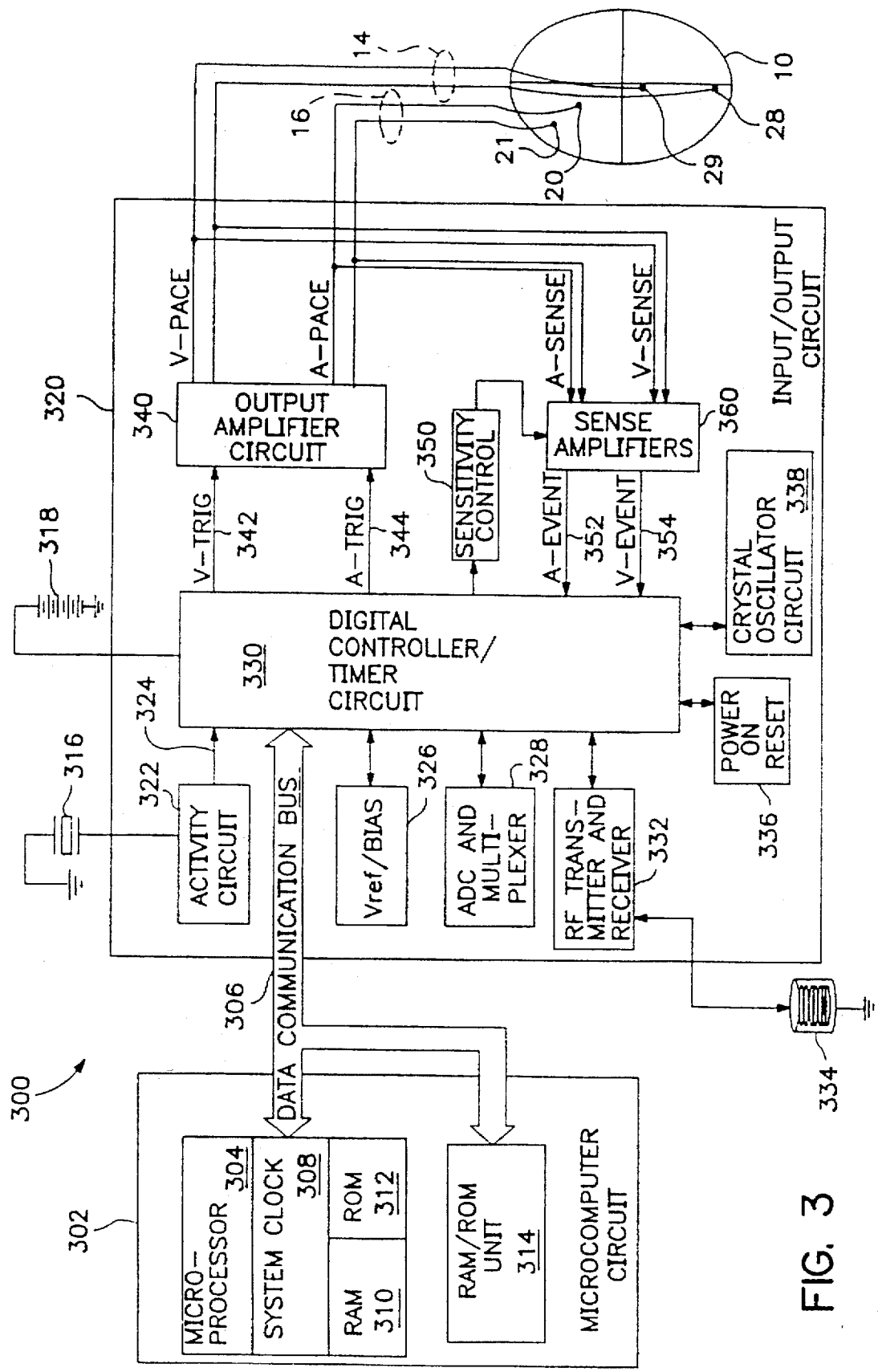
FIG. 3 is a block diagram of the primary functional components of a pacemaker used in the system and method of this invention.

FIG. 3 is a block functional diagram of the pacemaker illustrated in FIG. 1, as connected to a human heart 10. The circuitry illustrated is all located within the conductive housing or can 8 of the pacemaker, as illustrated in FIG. 1, and the bipolar leads 14 and 16 are illustrated schematically as coupled directly to the circuit. However, of course, in the actual device they would be coupled by means of removable electrical connectors inserted in the connector block 12, as illustrated in FIG. 1.

The pacemaker is divided generally into a microcomputer circuit 302 and a pacing circuit 320. A pulse generator circuit 340 includes a ventricular pulse generator circuit coupled to the heart 10 by means of electrodes 29 and 28 on lead 14, as well as an atrial pulse generator circuit coupled to the heart 10 by means of atrial electrodes 20 and 21, located on lead 16. Similarly, pacing circuit 320 includes atrial and ventricular sense amplifiers in sense amplifier circuit 360, coupled to the atrium and ventricle by means of leads 14 and 16 as well. The ventricular sense amplifier provides for separate detection and identification of QRS-wave signals, in a known manner; it may also provide for detection and identification of T-wave signals. The atrial sense amplifier provides for respective identification of P-waves and FFRS Far Field R-wave Signals. The output circuit 340 and sense amplifier circuit 360 may contain pulse generators and sense amplifiers corresponding to any of those presently employed in commercially marketed cardiac pacemakers. Control of timing and other functions within the pacemaker circuit is provided by digital controller/timer circuit 300, which includes a set of timers and associated logic. Digital controller/timer circuit 330 defines the basic pacing interval of the device, which may take the form of an A—A escape interval initiated on atrial sensing or pacing and triggering atrial pacing at the expiration thereof, or may take the form of a V—V escape interval, initiated on ventricular sensing or pacing and triggering ventricular pulse pacing at the expiration thereof. Digital controller/timer circuit 330 similarly defines the A-V escape interval, $AV_{ecs}$, discussed in detail below. The specific values of the intervals defined are controlled by the microcomputer circuit 302 by means of data and control bus 306. Sensed atrial depolarizations and FFRSs are communicated to the digital controller/timer circuit 330 on A event line 352; and ventricular depolarizations (QRS-waves) and repolarizations (T-waves) are communicated to the digital controller/timer circuit 330 on V event line 354. In order to trigger generation of a ventricular pacing pulse, digital controller/timer circuit 330 generates a trigger signal on V trig line 342. Similarly, in order to trigger an atrial pacing pulse, digital controller/timer circuit 330 generates a trigger pulse on a trig line 344.

Digital controller/timer circuit 330 also defines time intervals for controlling operation of the sense amplifiers in sense amplifier circuit 360. Typically, digital controller/timer circuit 330 will define an atrial blanking interval following delivery of an atrial pacing pulse, during which atrial sensing is disabled, as well as ventricular blanking intervals following atrial and ventricular pacing pulse delivery, during which ventricular sensing is disabled. Digital controller/timer circuit 330 will also define an atrial refractory period during which atrial sensing is disabled, this refractory period extending from the beginning of the A-V escape interval following either a sensed or paced atrial depolarization, and extending until a predetermined time following sensing of a ventricular depolarization or delivery of a ventricular pacing pulse. Digital controller/timer circuit 330 similarly defines a ventricular refractory period following ventricular sensing or delivery of a ventricular pacing pulse, which is typically shorter than the portion of the atrial refractory period following ventricular sensing or pacing. Digital controller/timer circuit 330 also controls sensitivity settings of the sense amplifiers 360 by means of sensitivity control 350. Control 350 is also utilized to generate timing windows for isolation and detection of portions of the received waves, e.g., FFRS signals from the atrial channel and R-wave and T-wave portions respectively from the ventricular channel.

In the embodiment illustrated in FIG. 2, the pacemaker is provided with a piezo electric sensor 316 which is intended to monitor patient activity, in order to allow provision of rate responsive pacing, such that the defined pacing rate (A—A escape interval or V—V escape interval) increases with increased demand for oxygenated blood. Sensor 316 generates electrical signals in response to sensed physical activity which are processed by activity circuit 322 and provided to digital controller/timer circuit 330. Activity circuit 332 and associated sensor 316 may correspond to the circuitry disclosed in U.S. Pat. No. 5,052,388, issued to Betzold et al., and U.S. Pat. No. 4,428,378, issued to Anderson et al. incorporated herein by reference in their entireties. Similarly, the present invention may be practiced in conjunction with alternate types of sensors such as oxygenation sensors, pressure sensors, pH sensors and respiration sensors, all well known for use in providing rate responsive pacing capabilities. Alternately, QT time may be used as the rate indicating parameter, in which case no extra sensor is required. Similarly, the present invention may also be practiced in non-rate responsive pacemakers.

Transmission to and from the external programmer 4 illustrated in FIG. 2 is accomplished by means of antenna 334 and associated RF transmitter and receiver 322, which serves both to demodulate received downlink telemetry and to transmit uplink telemetry. Crystal oscillator circuit 338 provides the basic timing clock for the circuit, while battery 318 provides power. Power on reset circuit 336 responds to initial connection of the circuit to the battery for defining an initial operating condition and similarly, resets the operative state of the device in response to detection of a low battery condition. Reference mode circuit 326 generates stable voltage reference and currents for the analog circuits within the pacing circuit 320, while analog to digital converter ADC and multiplexor circuit 328 digitizes analog signals and voltage to provide real time telemetry of cardiac signals from sense amplifiers 360, for uplink transmission via RF transmitter and receiver circuit 332. Voltage reference and bias circuit 326, ADC and multiplexor 328, power on reset circuit 336 and crystal oscillator circuit 338 may correspond to any of those presently used in current marketed implantable cardiac pacemakers.

Microcomputer circuit 302 controls the operational functions of digital controller/timer 330, specifying which timing intervals are employed, and controlling the duration of the various timing intervals, via data and control bus 306. Microcomputer circuit 302 contains a microprocessor 304 and associated system clock 308 and on processor RAM circuits 310 and 312, respectively. In addition, microcomputer circuit 302 includes a separate RAM/ROM chip 314. Microprocessor 304 is interrupt driven, operating in a reduced power consumption mode normally, and awakened in response to defined interrupt events, which may include delivery of atrial and ventricular pacing pulses as well as sensed atrial and ventricular depolarizations. In addition, if the device operates as a rate responsive pacemaker, a timed interrupt, e.g., every cycle or every two seconds, may be provided in order to allow the microprocessor to analyze the sensor data and update the basic rate interval (A—A or V—V) of the device. In addition, in a preferred embodiment of the invention, the microprocessor 304 may also serve to define variable A–V escape intervals and atrial and ventricular refractory periods which may also decrease in duration along with decreases in duration of the basic rate interval. Specifically, the microprocessor is used to carry out the routines illustrated in FIGS. 4A, 4B, 5A and 5B.

The illustrated circuitry of FIG. 3 is merely exemplary, and corresponds to the general functional organization of most microprocessor controlled cardiac pacemakers presently commercially available. It is believed that the present invention is most readily practiced in the context of such a device, and that the present invention can therefore readily be practiced using the basic hardware of existing microprocessor controlled dual chamber pacemakers, as presently available, with the invention implemented primarily by means of modifications to the software stored in the ROM 312 of the microprocessor circuit 302. However, the present invention many also be usefully practiced by means of a full custom integrated circuit, or any combination of hardware and software.

Figure 4A:
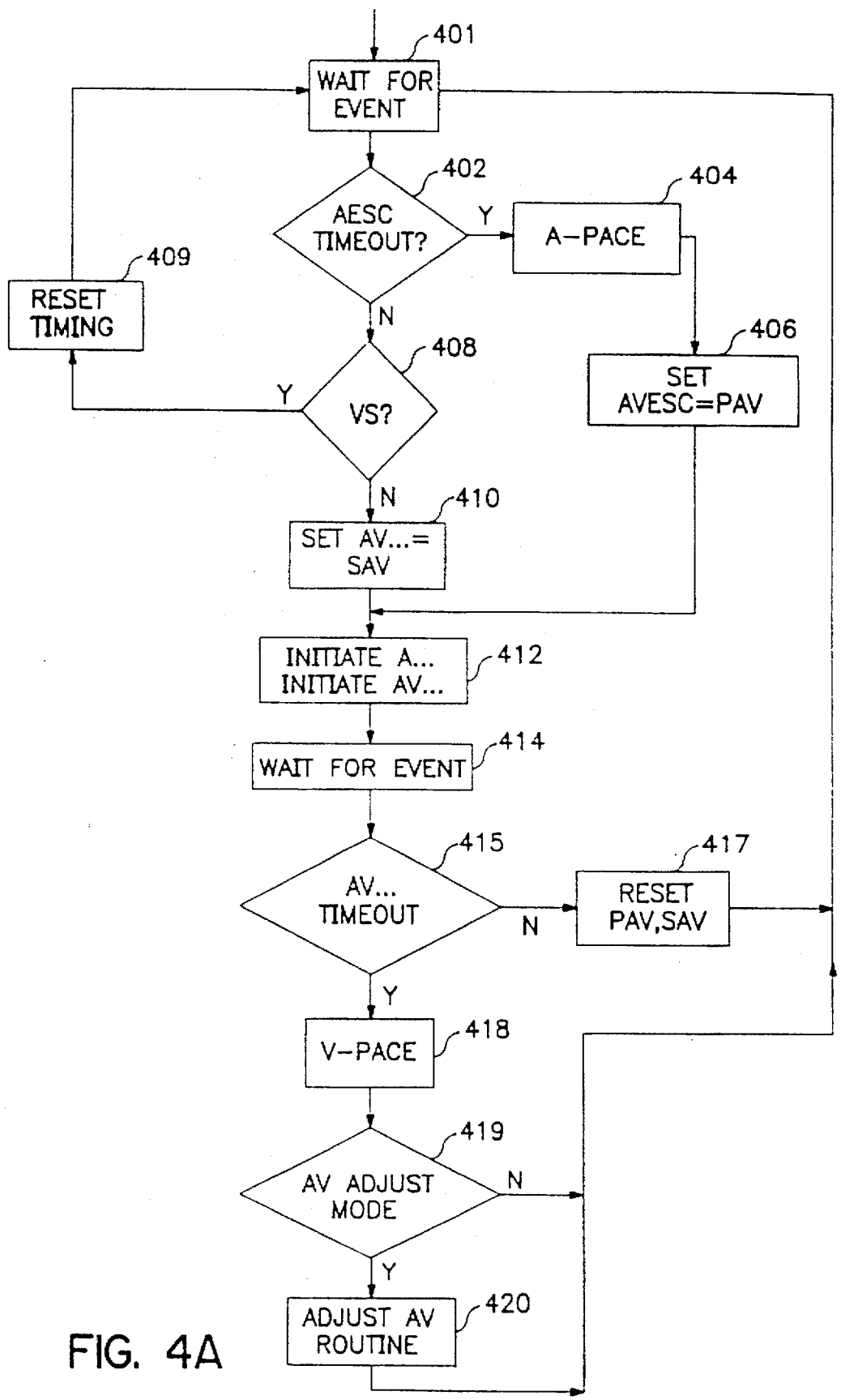
FIG. 4A is a generalized flow diagram illustrating steps taken in synchronous pacing in accordance with this invention, including adjusting AV escape interval for optimizing HOCM therapy.

Referring now to FIG. 4A, there is shown a generalized flow diagram of steps taken by a pacemaker system in accordance with this invention in performing synchronous pacing, with adjustment of $AV_{esc}$ for optimal HOCM therapy. The steps of this flow diagram are suitably carried out by microcomputer circuit 302. This is a simplified flow diagram setting forth only steps pertinent to controlling $AV_{esc}$, and does not include many other steps and responses that occur during each cycle of a typical dual chamber pacemaker. The illustrated logic of FIG. 4A recognizes that the intrinsic AV conduction time following an atrial pace pulse is greater than following a sensed atrial depolarization, by an amount described as "atrial sense offset", or ASO in a referenced U.S. application Ser. No. 08/214,933. The $AV_{esc}$ following an atrial pace is defined as PAV; the $AV_{esc}$ following an atrial sense is defined as SAV; and PAV=SAV+ASO.

At block 401, the routine of FIG. 4A is waiting for what is expected to be an atrial event. When an event occurs, the routine goes to block 402 and determines whether there has been timeout of the atrial escape interval, $A_{esc}$. If yes, this indicates that an atrial pace (AP) should be delivered, and this is done at block 404. Following this, the routine sets $AV_{esc}$ to PAV, and initiates timeout of $AV_{esc}$. Returning to 402, if there has been no timeout of $A_{esc}$, the pacemaker proceeds to 408, and determines whether there has been an early ventricular sense (VS). If yes, the routine branches to block 409 and resets the timing appropriately, whereafter it returns to block 401. However, as would normally be the case, if at 408 the event is not a VS, meaning that it has been an atrial sense (AS), the routine proceeds to block 410 and sets $AV_{esc}$ to the current value of SAV. Following this, the routine goes to 412 and initiates timeout of the atrial escape interval ($A_{esc}$), and timeout of the AV escape interval, $AV_{esc}$ (either SAV or PAV). Then, at 414, the pacer waits for the next event, normally a ventricular event.

At 415, the pacemaker responds to an event by first determining whether the event was a timeout of $AV_{esc}$. If no, meaning that there was a ventricular sense, the pacemaker proceeds to block 417 and resets PAV and SAV to a shorter value which ensures capture by the next ventricular pace pulse. For example, each of these values can be decremented by 20 or 50 ms, to ensure that succeeding timeouts of $AV_{esc}$ occur early enough for complete capture. It is to be noted, however, that the algorithms discussed below are designed to avoid an occurrence of VS, such that the pacemaker should rarely take this path.

If at 415 there has been a timeout of $AV_{esc}$, then the pacemaker proceeds to block 418 and delivers a V pace. Then, at block 419, the pacemaker determines whether it is programmed to go into the AV adjust routine. If no, the routine is done and it exists back to 401. If yes, the pacemaker goes to the adjust AV routine at block 420. Here, the pacemaker analyzes collected data, e.g., VP-FFRS time; FFRS duration; or FFRS or QRS amplitude. With this data in hand, the pacemaker system can adjust the values of PAV and SAV, in accordance with a predetermined algorithm for changing $AV_{esc}$ so as to optimize resultant pre-excitation. Following this, the routine returns to block 401 and waits for the next atrial event.

Note that the pacemaker can be programmed for automatically monitoring AV data and adjusting $AV_{esc}$ each pacemaker cycle, or these steps can be taken on some other periodic or user-programmed basis, within the scope of the invention. For an implanted pacemaker which is set to automatically adjust AV, the pacemaker goes directly to 420. Similarly, for a pacemaker system in accordance with this invention which adapted to be programmed specifically by a physician, the routine exits unless the programming sequence has been activated.

Figure 4B:
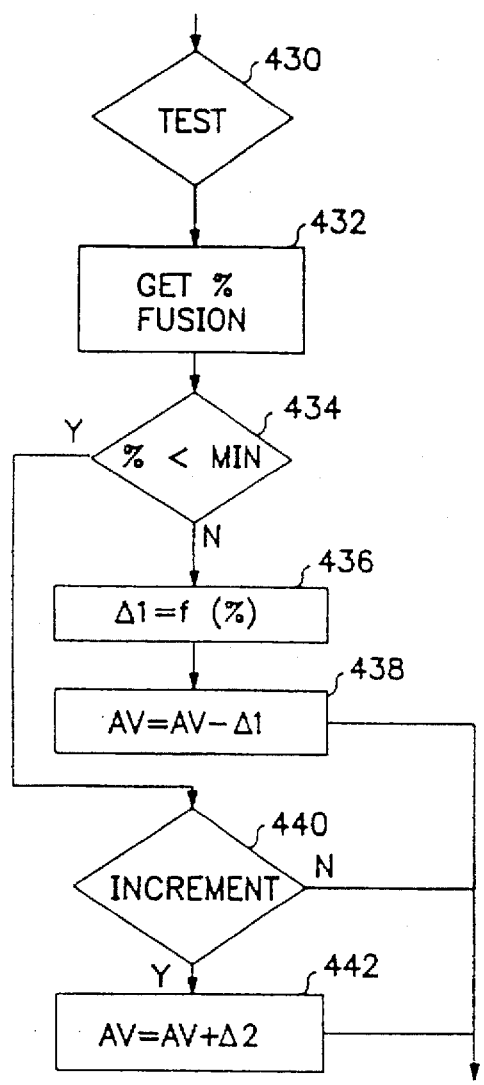
FIG. 4B is a flow diagram of a generalized routine used by the pacemaker system of this invention in adjusting the AV escape interval for optimized HOCM therapy pacing.

FIG. 4B is a simplified flow diagram showing the primary steps of a generalized routine for controlling AV escape interval as a function of determined percentage. At 430, it is determined whether the pacemaker is programmed to go into the test to determine whether AV escape interval should be changed. The programmer may be permanently set to conduct a test repetitively, or may be programmed from an external programmer by a physician. Assuming that the pacemaker is so programmed, at 432 the pacemaker runs a routine to get the percentage fusion. This routine is illustrated in greater detail in connection with FIGS. 5, 6A and 6B. After this, at block 434, it is determined whether the percentage is less than a predetermined minimum, e.g., less than 0.5%, 1%, 2%, etc. If yes, meaning that the number of fusion beats is acceptably low, the routine branches to block 440, and determines whether to increment AV escape interval. This decision is preferably made as a function of the detected percentage. For example, if the percentage is 0, the decision is made to increment, and at 442 AV is incremented by a small amount $\Delta 2$, e.g., 5 ms.

Returning to decision block 434, if the percentage is not less than the predetermined minimum, the routine goes to block 436 and determines a decrement amount $\Delta 1$ as a function of the detected percentage. Thus, for example, if the percentage is relatively high, $\Delta 1$ can be set to a relatively higher figure, e.g., in the range of 20–50 ms. If the percentage is lower, $\Delta 1$ may be more suitably set to a figure in the range of 5–10 ms. Then, at 438 AV is decremented by $\Delta 1$, and the routine exits.

Figure 5:
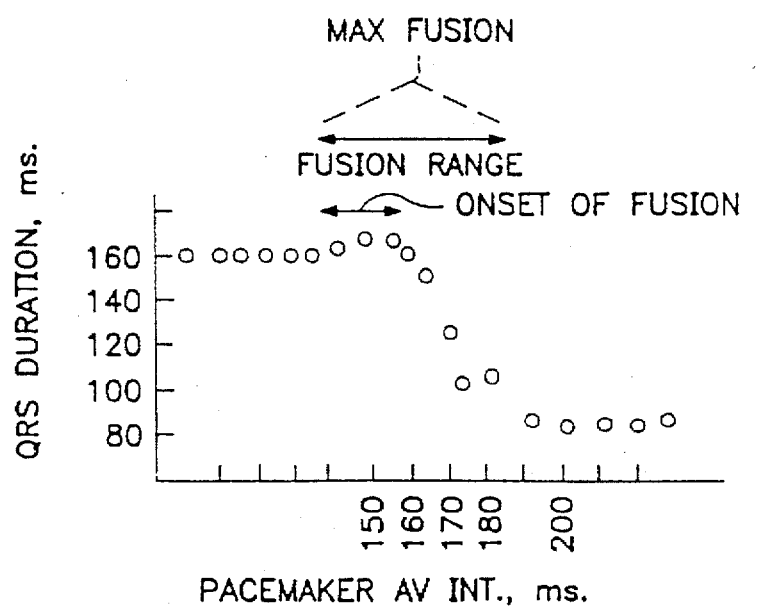
FIG. 5 is a representative data plot of QRS duration as a function of pacemaker AV interval.

Referring now to FIG. 5, there is shown a plot of data representative of QRS or FFRS duration (ms) as a function of pacemaker AV interval (ms). As seen in FIG. 5, the QRS duration is relatively low at higher AV intervals which are greater than the patient's intrinsic PR conduction time, i.e., where a VS occurs before timeout of $AV_{esc}$. However, as $AV_{esc}$ is shortened, it comes into a fusion area where QRS increases and peaks; at shorter intervals, where a VP results in full capture, QRS duration is substantially constant at a value higher than the values corresponding to spontaneous QRSs. The knee portion between full capture and failure to capture is termed the fusion area, or range, and the ability to detect duration changes in this area provides the basis for one embodiment of this invention. As used herein, the term "fusion" embraces the entire range, including the lower portion of the range referred to as "onset of fusion." In the discussions of FIGS. 6A and 6B below, detection of fusion may be determined by examination of QRS duration to see whether operation is within the fusion range, or any part of it. Alternately, fusion may be determined by comparing other QRS characteristics, such as morphology and amplitude. Additionally, fusion may be determined by detection of changes in the ventricular repolarization, or T-wave, as well as changes in the VP-QRS time, i.e., the time interval between delivery of a ventricular pace pulse and the evoked QRS.

Still referring to FIG. 5, it is noted that there is a variation in the degree of fusion within the fusion range. Thus, there is maximal fusion toward the center of the range, and minimal fusion toward the upper and lower limits of the range. It is within the scope of the invention to measure the degree of fusion, and control as a function of the degree of fusion. For example, a beat with no greater than X% fusion can be deemed acceptable, such that the algorithm would allow a maximum of Y% of the beats to have greater than X% fusion.

Figure 6B:
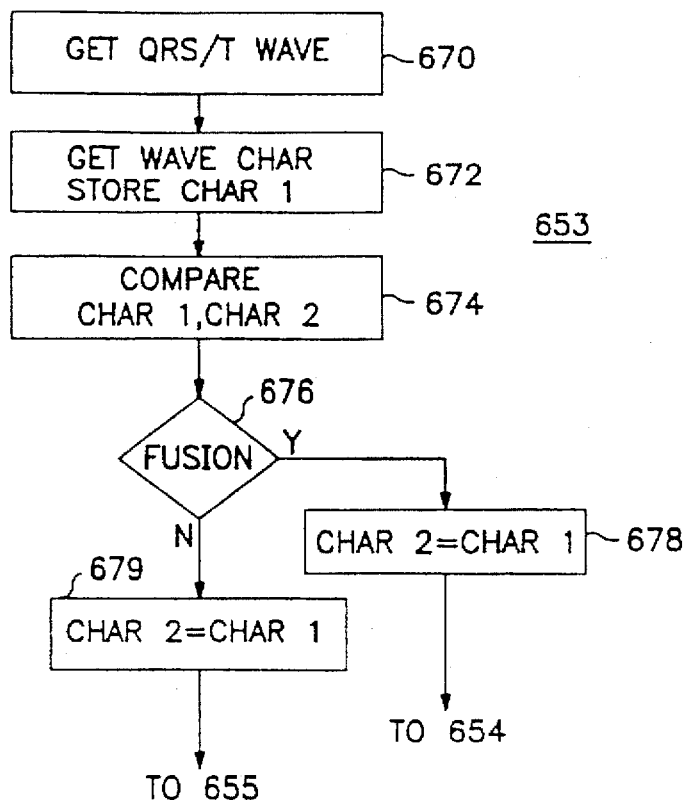
FIG. 6B is a simplified flow diagram showing steps for detecting the occurrence of a fusion beat.
Figure 6A:
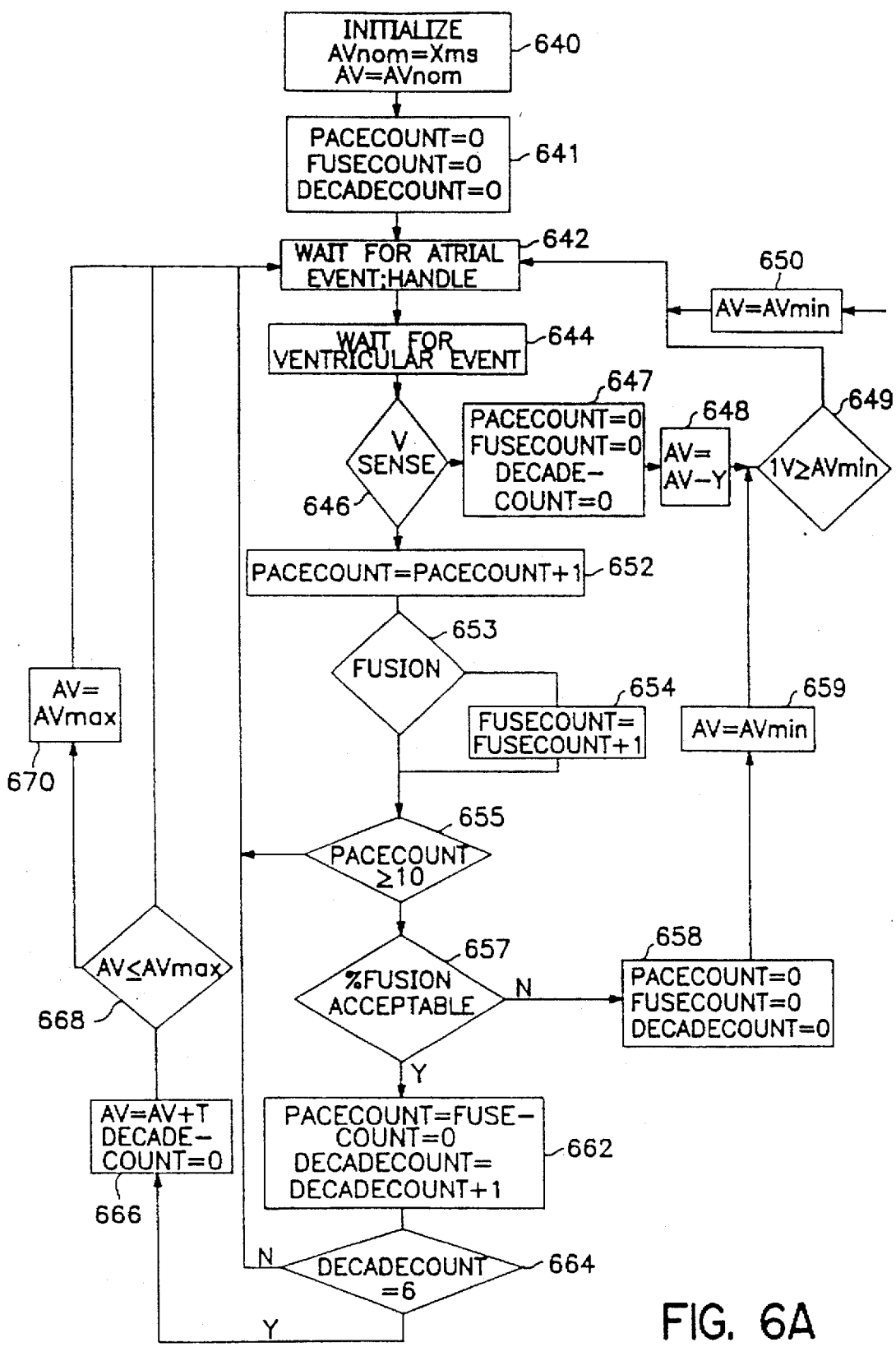
FIG. 6A is a detailed flow diagram of a routine of the pacemaker system of this invention for adjusting AV escape interval as a function of a determined percentage of detected fusion beats.

Referring now to FIG. 6A, the routine is initially entered at 640, where the AV interval is set equal to a nominal predetermined value. At 641 three routine variables are set equal to 0, namely PACECOUNT, FUSECOUNT, and DECADECOUNT. Following this, the routine goes to block 642, and waits for an atrial event, either sense or pace. The pacemaker sets $AV_{esc}$, as illustrated in FIG. 4A, and proceeds to block 644 where it waits for a V event, either sense or pace. At 646, if the V event has been a sense, the routine branches to 647 and sets the three routine variables to 0. Thereafter, at 648, the AV interval is decremented by a predetermined value Y, to bring the interval back to a shorter value so as to ensure synchronous pacing with capture. At 649 the pacemaker checks to see if the new value of AV interval is equal to or greater than a programmed value $AV_{MIN}$ and adjusts the value if necessary at 650 before returning to the wait for the next atrial event.

If, at 646, it is determined that there has been a delivered ventricular pace pulse, then at 652 the variable PACECOUNT is incremented by 1. Then, at 653, the pacemaker system waits for an evoked response, and determines whether there has been a fusion beat. As discussed previously, fusion can be determined in a number of different ways. In the preferred embodiment, fusion is determined by detecting a significant decrease in duration of either the QRS waveform from the V sense channel, or the FFRS waveform from the A sense channel. Reference is made to FIG. 6B, and the discussion relating thereto. If fusion is detected, the variable FUSECOUNT is incremented at 654. Then, at 655 the value of PACECOUNT is compared to a predetermined number, e.g. 10. If PACECOUNT has not reached the predetermined number, the routine returns to 642. However, if it has, the routine goes to 657 and determines the percent of fusion beats in the last n cycles (e.g., 10), and whether this percentage is acceptable. If no, the routine branches to 658, resets the three routine variables to 0, and then at 659 decrements AV by a fixed amount indicated as Z. Z, for example, may be in the range of 20–50 ms, chosen to shorten AV interval so that it is safely short of the value where fusion has been detected.

Returning to 657, if the percent fusion occurrences is acceptable, e.g., there have been no fusion beats or less than the minimum acceptable percentage, the routine goes to 662 and sets PACECOUNT and FUSECOUNT equal to 0. DECADECOUNT is incremented by 1, and then at 664 the DECADECOUNT is compared to a fixed number, illustrated as 6. A DECADECOUNT of 6 is seen to correspond to 60 cycles in this example. If the DECADECOUNT count has not reached 6, the routine returns to 642. However, if it has, this means that pacemaker activity has remained quiescent for a predetermined number of cycles, and the routine reacts by adjusting $AV_{esc}$ so as to search for a fusion value of the AV interval. The routine goes to 666 and increments $AV_{esc}$ by a variable T, suitably 5 ms, which takes it toward the fusion range. DECADECOUNT is set back to 0. Then, at 668 AV is compared to $AV_{MAX}$, and is set equal to $AV_{MAX}$ at 670 if required. It is seen that in this manner, as long as no unacceptable fusion percentage is detected, the AV interval is periodically incremented toward a fusion value, thereby providing a closed loop control for keeping the value of AV escape interval within a short range. The range of $AV_{esc}$ has a high limit at about the onset of fusion, and is dynamic so as to track with time any changes in the patient's intrinsic conduction interval.

Referring now to FIG. 6B, there is shown a simplified flow diagram for determining whether a fusion beat has occurred. At 670, the pacemaker gets the QRS or T-wave, and examines the wave at 672 to obtain a wave characteristic. As discussed above, this characteristic may be duration, as illustrated in FIG. 5, or any other signature type characteristic. The data reflecting the characteristic are stored with the identification CHAR1. Then, at 674, the pacemaker compares the characteristic data just obtained (CHAR1) with the characteristic data of the prior signal designated as CHAR2. Based on this comparison, at 676, the pacemaker makes a determination as to whether or not a fusion beat has just occurred. Then, CHAR 2 is set equal to the just obtained CHAR 1 at 678 or 679, for use during the next cycle. The steps of obtaining characteristics at 672 are accomplished by use of standard hardware, preferably also using digital processing techniques. For determining QRS width, or duration, this signal is processed to determine when it first rises to a predetermined level, and when it falls back below such level. Amplitude is suitably measured by either a simple peak detector or other standard amplitude detection circuitry. For getting the time of VP-QRS, a standard edge detector may be utilized in circuit 330 to sense when the leading edge of the QRS signal has reached the predetermined level, or has increased by a predetermined percentage. These standard circuits may be supplemented or replaced by known digital processing techniques carried out with the aid of microprocessor system 302. Note also that fusion can be determined by comparing the wave characteristic with a standard wave, i.e., a reference characteristic, taken from a full capture wave evoked by a ventricular pace pulse delivered after a short $AV_{esc}$.

It is to be noted that while the preferred embodiment has been illustrated in terms of determining the percentage of fusion beats that is acceptable, similar arrangements are within the scope of the invention. Thus, the algorithm for determining whether the number of fusion beats is acceptable or non-acceptable may involve any desired degree of complexity. For example, the determination may be made on the basis of total accumulated fusion beats over a predetermined time interval, e.g., on a daily basis. Alternately, the percentage of fusion beats that is acceptable may be adjusted in accordance with monitored patient history, and likewise the adjustment following a determination of an unacceptable fusion rate may be varied as a function of patient history.

While the preferred embodiments of the invention had been described with reference to dual chamber pacemakers, and control of the AV escape interval, the therapy provided by this invention can also be provided by a pacemaker system which is operating in a non-tracking, or asynchronous mode. For example, in dual chamber pacemakers with a "Modeswitching" feature, the pacing mode is automatically changed from an atrial tracking mode (VDD, DDD, DDDR) to a non-tracking mode (DDIR or VVIR) upon detection of an atrial arrhythmia. In these situations, the pacemaker cannot track the atrial signal because the atrial rate is too high; and if AV conduction is intact, the pacemaker does not pace the ventricle because the intrinsic conduction is too fast and the ventricular pace pulse is inhibited. However, when a pacemaker is in a single chamber ventricular (VVI, VVIR) or dual chamber non-tracking mode (DDI, DDIR), the pacemaker system can nonetheless perform an analogous operation to the dual chamber therapy described above, except that the pacemaker system controls ventricular pacing escape interval ($V-V_{esc}$) rather than $AV_{esc}$. In such an embodiment, $V-V_{esc}$ is initially shortened to correspond to a relatively high ventricular rate when tracking is not available, and with time $V-V_{esc}$ is lengthened until fusion occurs. Thus, the algorithm is basically the same as for the above examples where $AV_{esc}$ is modified, except control is through the V—V escape interval.

Figure 7:
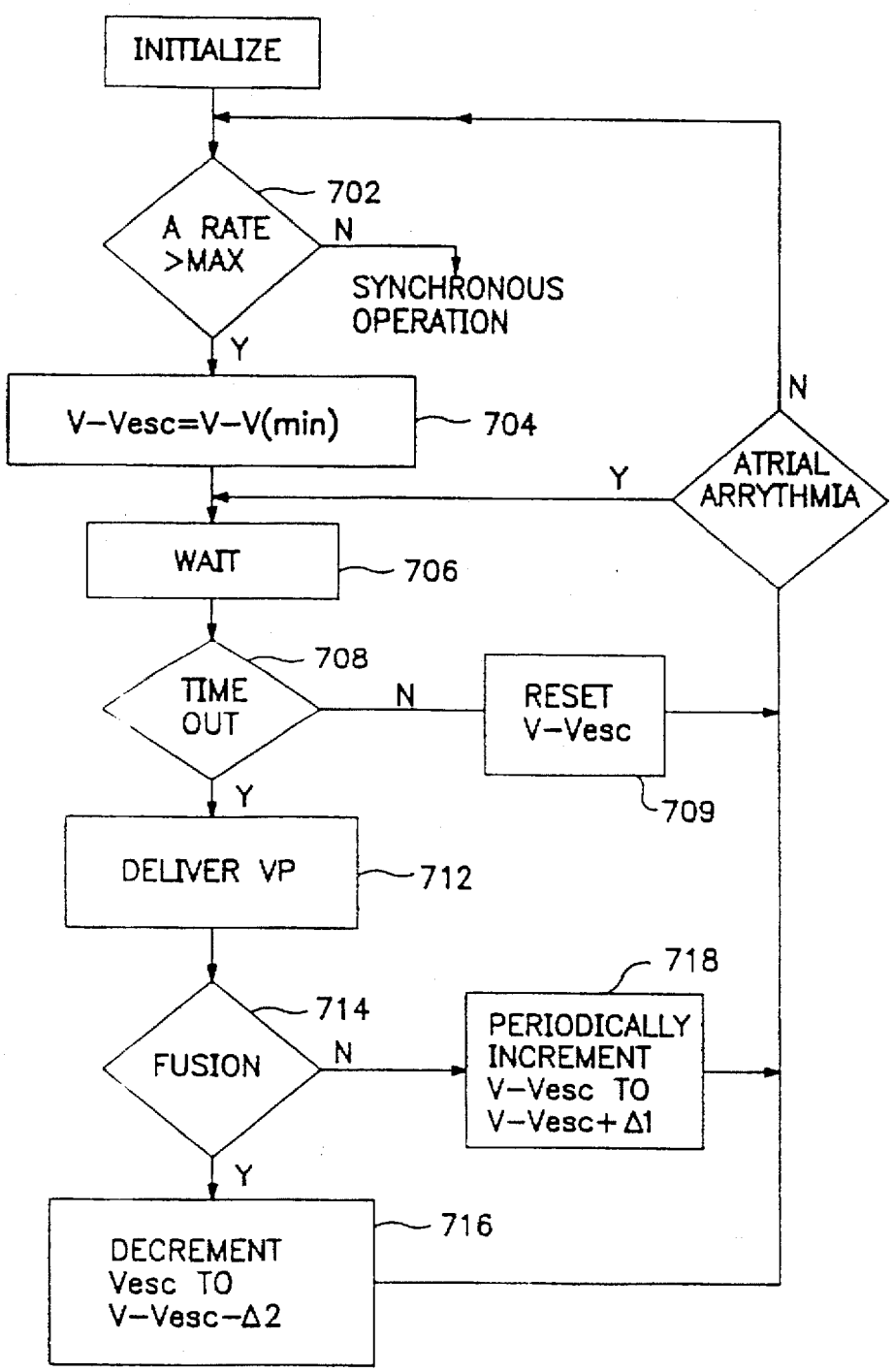
FIG. 7 is a simplified flow diagram of a routine of an alternate embodiment of the pacemaker system of this invention for adjusting V—V escape interval for providing pacing therapy in a non-tracking mode.

Referring to FIG. 7, there is shown a simplified flow diagram for carrying out single chamber mode pacing therapy for patients with cardiomyopathy. It is noted that the pacemaker system monitors the atrial rate each cycle, although this is not shown in the diagram of FIG. 7. At 702, it is determined whether the atrial rate is greater than a maximum rate, such that it is too high. If no, the system branches to synchronous operation. However, if the atrial rate is found to be too high, or some other arrhythmia is detected at 702, the routine goes to block 704 and sets $V-V_{esc}$ to a minimum value. Note that in a more sophisticated flow diagram the escape interval may be gradually ramped toward the minimum value, corresponding to a maximum asynchronous rate. At 706, the pacemaker waits for an event, and at 708 determines whether the event has been a timeout of a $V-V_{esc}$. If no, meaning that a natural ventricular depolarization was sensed, $V-V_{esc}$ is reset at 709; if the arrhythmia is continuing, the routine returns to wait at block 706. However, if there has been a timeout, a ventricular pace pulse is delivered at 712, and then at 714 the pacemaker system determines whether this has resulted in a fusion beat. If no, the routine branches through 718, where periodically $V-V_{esc}$ is incremented by $\Delta 1$. This increment can be done cyclically, or every N cycles, or by any other programmed arrangement. If fusion has been determined, at block 716 the pacemaker decrements $V-V_{esc}$ by subtracting $\Delta 2$. By this arrangement, the pacemaker varies the rate of the delivered asynchronous pulses so as to optimize pre-excitation in the same manner as discussed above for dual chamber-atrial tracking mode therapy. Following block 716 or 718, the routine checks to see if the arrhythmia is still present. If the pacemaker determines, at block 720, that the arrhythmia is over, then the program branches back to block 702.

It is noted that the embodiment of FIG. 7 can be practiced with alternate techniques for determining when $V-V_{esc}$ should be adjusted. Thus, steps 714 and 716 can be eliminated, the routine periodically increasing $V-V_{esc}$ at 718 until a VS occurs, whereupon $V-V_{esc}$ is decremented to regain pacing. Thus, the scope of the FIG. 7 embodiment is not limited to the preferred technique of detecting the occurrence of fusion in order to control the timing of delivered pace pulses.

What is claimed is:

1. A method of operating a pacemaker in a non-tracking mode adapted to apply when said pacemaker is implanted in a patient with a heart having atrial events, comprising:
   (a) delivering ventricular pace pulses to a patient without a timed relationship to atrial events,
   (b) lengthening a V—V escape interval of delivered ventricular pace pulses, and determining when one or more said lengthened interval delivered ventricular pace pulses fail to result in fall capture of the ventricle, and
   (c) shortening said V—V escape interval in response to a determination of such a failure.

2. The method as described in claim 1, comprising detecting a rate of the patient's spontaneous atrial beats, detecting when the atrial rate is above a predetermined atrial high rate limit, and initiating steps a, b and c as set forth in claim 1 upon detecting an atrial rate above said high rate limit.

3. The method as described in claim 2, comprising operating said step a so as to initiate delivery of said ventricular pace pulses at a predetermined ventricular high rate limit upon said detecting of said atrial rate above said atrial high rate limit.

4. The method as described in claim 3, further comprising limiting the duration of pacing at said ventricular high rate limit.

5. The method as described in claim 4, wherein said lengthening step comprises increasing said V—V escape interval over an extended period of time at regular intervals longer than every consecutive beat.

6. The method of pacing therapy as described in claim 1, comprising determining a fusion beat by comparing a characteristic of a QRS wave evoked by a ventricular pace pulse to a reference QRS wave characteristic.

7. The method of pacing therapy as described in claim 1, wherein said determining step comprises determining when a delivered pace pulse results in a fusion beat.

8. The method as set forth in claim 5 wherein step c further comprises increasing the V—V escape interval when a fusion beat is detected.

9. The method of claim 5 wherein step c further comprises increasing the V—V escape interval only upon detection of more than a predetermined number of fusion beats over a predetermined period.

10. The method of claim 1 further comprising detection of fusion beats and reacting to such detection by increasing the V—V escape interval.

11. A method of operating a pacemaker in a non-tracking mode adapted to apply when said pacemaker is implanted in a patient with a heart having atrial events, comprising:

detecting a rate of the patient's spontaneous atrial beats, detecting when the atrial rate is above a predetermined atrial high rate limit, and upon detecting an atrial rate above said high rate limit;

(a) delivering ventricular pace pulses to a patient without a timed relationship to detected atrial events, (b) changing a V—V escape interval of delivered ventricular pace pulses, and determining when one or more said changed interval delivered ventricular pace pulses fail to result in full capture of the ventricle, and (c) shortening said V—V escape interval in response to a determination of such a failure.

* * * * *